US010494452B2

(12) United States Patent
Zhao et al.

(10) Patent No.: US 10,494,452 B2
(45) Date of Patent: Dec. 3, 2019

(54) LOW-MOLECULAR-WEIGHT GLYCOSAMINOGLYCAN DERIVATIVE CONTAINING TERMINAL 2, 5-ANHYDRATED TALOSE OR DERIVATIVE THEREOF

(71) Applicant: Jiuzhitang Co., Ltd., Changsha, Hunan (CN)

(72) Inventors: Jinhua Zhao, Yunnan (CN); Mingyi Wu, Yunnan (CN); Na Gao, Yunnan (CN); Zi Li, Yunnan (CN); Sensen Lai, Yunnan (CN); Longyan Zhao, Yunnan (CN)

(73) Assignee: Jiuzhitang Co., Ltd., Changsha (CN)

( * ) Notice: Subject to any disclaimer, the term of this patent is extended or adjusted under 35 U.S.C. 154(b) by 155 days.

(21) Appl. No.: 14/779,934

(22) PCT Filed: Dec. 20, 2013

(86) PCT No.: PCT/CN2013/090124
§ 371 (c)(1),
(2) Date: Sep. 24, 2015

(87) PCT Pub. No.: WO2014/166282
PCT Pub. Date: Oct. 16, 2014

(65) Prior Publication Data
US 2016/0060364 A1  Mar. 3, 2016

(30) Foreign Application Priority Data
Apr. 12, 2013  (CN) .......................... 2013 1 0127447

(51) Int. Cl.
C08B 37/00 (2006.01)
C07H 5/06 (2006.01)
A61K 31/726 (2006.01)
A61K 9/00 (2006.01)
A61K 9/08 (2006.01)
A61K 9/19 (2006.01)

(52) U.S. Cl.
CPC ........ *C08B 37/0063* (2013.01); *A61K 9/0019* (2013.01); *A61K 9/08* (2013.01); *A61K 9/19* (2013.01); *A61K 31/726* (2013.01); *C07H 5/06* (2013.01)

(58) Field of Classification Search
None
See application file for complete search history.

(56) References Cited

U.S. PATENT DOCUMENTS 4,351,938 A  9/1982  Barnett
2012/0270834 A1* 10/2012  Zhao ................... A61K 31/737
514/54

FOREIGN PATENT DOCUMENTS

CN  1531555 A  9/2004
CN  1997657 A  7/2007
CN  103214591 A  7/2013

OTHER PUBLICATIONS

Edward Conrad, H. (2001). Degradation of heparan sulfate by nitrous acid. Proteoglycan Protocols, 347-351.*
Zhang, Y., Iwasa, T., Tsuda, M., Kobata, A., & Takasaki, S. (1997). A novel monoantennary complex-type sugar chain found in octopus rhodopsin: occurrence of the Galß? 4Fuc group linked to the proximal N-acetylglucosaniine residue of the trimannosyl core. Glycobiology, 7(8), 1153-1158. (Year: 1997).*
Brown, G. M., Huckerby, T. N., Morris, H. G., & Nieduszynski, I. A. (1992). Degradation of articular cartilage keratan sulphates using hydrazinolysis and nitrous acid. Environment of fucose residues. Biochemical Journal, 286(Pt 1), 235. (Year: 1992).*
Wu, M., Huang, R., Wen, D., Gao, N., He, J., Li, Z., & Zhao, J. (2012). Structure and effect of sulfated fucose branches on anticoagulant activity of the fucosylated chondroitin sulfate from sea cucumber Thelenata ananas. Carbohydrate Polymers, 87(1), 862-868. (Year: 2012).*
Zhao et al., (2013). Structure and anticoagulant activity of fucosylated glycosaminoglycandegraded by deaminative cleavage. Carbohydrate Polymers, 98 (2013) 1514-1523. doi:/10.1016/j.carbpol.2013. 07.063 (10 pages).
Wu, M., Xu, S., Zhao, J., Kang, H., & Ding, H. (2010). Preparation and characterization of molecular weight fractions of glycosaminoglycan from sea cucumber Thelenata ananas using free radical depolymerization. Carbohydrate Polymers, 345(5), 649-655. doi:10.1016/j.carres. 2009.11.030 (7 pages).
Shaklee, P., & Conrad, H. (1986). The disaccharides formed by deaminative cleavage of N-deacetylated glycosaminoglycans. Biochemical Journal, 235, 225-236. doi:10.1042/bj2350225 (12 pages).
Lever & Page, "Novel Drug Development Opportunities for Heparin," Nature Reviews Drug Discovery,2002,1:140-148.
Mende et al., "Chemical Synthesis of Glycosaminoglycans," Chemical Reviews, 2016, 116: 8193-8255.
Mourão et al., "Structure and Anticoagulant Activity of a Fucosylated Chondroitin Sulfate from Echinoderm," J. Biol. Chem., 1996, 271(39): 23973-23984.
Vieira et al., "Structure of a Fucose-branched Chondroitin Sulfate from Sea Cucumber," J. Biol. Chem., 1991, 266 (21):13530-13536.
Gerbst et al., "Conformational Analysis of the Oligosaccharides Related to Side Chains of Holothurian Fucosylated Chondroitin Sulfates," Mar. Drugs, 2015, 13: 936-947.

(Continued)

*Primary Examiner* — Dale R Miller
(74) *Attorney, Agent, or Firm* — Maschoff Brennan

(57) ABSTRACT

A low-molecular-weight fucosylated glycosaminoglycan (aTFG) containing 2,5-anhydrated talose, alditol, glycosylamine or N-substituted glycosylamine monosaccharide composition thereof, preparation method thereof, pharmaceutical compositions containing the aTFG, and use thereof for preventing and/or treating thrombotic diseases are provided. The aTFG has potent anticoagulant activity targeting at intrinsic coagulation factor Xase, and inhibiting thrombogenesis, and therefore can be used as drugs for preventing and/or treating cardiovascular and cerebrovascular diseases.

7 Claims, 7 Drawing Sheets

(56) References Cited

OTHER PUBLICATIONS

Panagos et al., "Fucosylated Chondroitin Sulfates from the Body Wall of the Sea Cucumber Holothuria forskali," J. Biol. Chem., 2014, 289(41): 28284-28298.

Zhao et al., "Structure and anticoagulant activity of fucosylated glycosaminoglycan degraded by deaminative cleavage," Carbohyd Polym, 2013, 98, 1514-1523.

Zhao et al., "Discovery of an intrinsic tenase complex inhibitor: Pure nonasac,charide from fucosylated glycosaminoglycan," Pro. Natl. Acad. Sci. USA 2015, 112, 8284-8289.

Wu et al., "Anticoagulant and antithrombotic evaluation of native fucosylated chondroitin sulfates and their derivatives as selective inhibitors of intrinsic factor Xase," Eur J Med Chem. 2015, 92:257-269.

Shively, J. E, & Conrad, H. E., "Formation of anhydrosugars in chemical depolymerization of heparin." Biochemistry, 1976, 15(18), 3932-3942.

Seth and Fanayan, "Mass Spectrometry-Based N-Glycomics of Colorectal Cancer," Int. J. Mol. Sci. 2015, 16(12), 29278-29304.

Caterson et al.,"Keratan sulfate, a complex glycosaminoglycan with unique functional capability," Glycobiology, 2018, 28(4):182-206.

Santos et al, "Exploring the structure of fucosylated chondroitin sulfate through bottom-up nuclear magnetic resonance and electrospray ionization-high-resolution mass spectrometry approaches", Glycobiology. 2017, 27(7), 625-634. p. 626.

Wu et al., "Free-radical depolymerization of glycosaminoglycan from sea cucumber Thelenata ananas by hydrogen peroxide and copper ions", CarbohydrPolym. 2010, 80, 1116-1124.

Wu et al., "Depolymerization of fucosylated chondroitin sulfate from sea cucumber,Pearsonothuria graeffei, via 60Coirradiation", CarbohydrPolym. 2013, 93,604-614.

Gao et al., "B-Eliminative depolymerization of the fucosylated chondroitin sulfate and anticoagulant activities of resulting fragments", CarbohydrPolym. 2015, 127, 427-437.

Guo & Conrad. "The Disaccharide Composition of Heparins and Heparan Sulfates", Anal Biochem. 1989, 176(1), 96-104.

Shang et al., "Precise structures of fucosylated glycosaminoglycan and its oligosaccharides as novel intrinsic factor Xase inhibitors", Eur J Med Chem. 2018, 148, 423-435.

Yin et al., "Oligosaccharides from depolymerized fucosylated glycosaminoglycan: structures and minimum size for intrinsic factor Xase complex inhibition", J Biol Chem. 2018, 293(36),14089-14099.

* cited by examiner

LOW-MOLECULAR-WEIGHT GLYCOSAMINOGLYCAN DERIVATIVE CONTAINING TERMINAL 2, 5-ANHYDRATED TALOSE OR DERIVATIVE THEREOF

FIELD OF THE INVENTION

The present invention belongs to the field of medical technology, and particularly relates to a low-molecular-weight fucosylated glycosaminoglycan containing terminal 2,5-anhydrated talose or derivative thereof (2,5-anhydrated Talose terminal Low-molecular-weight Fucosylated Glycosaminoglycan, aTFG), preparation method thereof, pharmaceutical compositions containing said aTFG, and the use thereof for preventing and/or treating cardiovascular and cerebrovascular diseases.

BACKGROUND OF THE INVENTION

Cardiovascular and cerebrovascular diseases have high incidence rate, high disability rate, high mortality rate, high recurrence rate and many complications, which seriously threatening people's health and quality of life. Thrombosis is one of the major causes of cardiovascular and cerebrovascular diseases. Antithrombotic drugs including anticoagulants are the first-line drugs in clinical for the treatment of cardiovascular diseases, and occupy an important position in the medicine market. The anticoagulant drugs mainly include coumarin anticoagulants and heparin anticoagulants, which have definite pharmacodynamical effect and pharmacological mechanism, but also have obvious clinical application defects: the defects of the anticoagulant drugs include severe bleeding tendency, slow onset and large individual differences due to their inhibition of synthesis of series of coagulation factors; heparin mainly target at the coagulation factors IIa and Xa (f.IIa, f.Xa) in the common pathway of the coagulation cascade, and the major defects of the drugs are serious bleeding risk and thrombocytopenia associated with their targets. Therefore, a new type anticoagulant drug, which has an advantage on pharmacological and pharmacodynamic action, is needed for clinical. The core of developing a new type anticoagulant drug is to avoid bleeding tendency efficiently; however, a breakthrough progress has not been made in the research of the innovative drugs with low bleeding tendency.

Fucosylated glycosaminoglycan (FGAG) from an echinoderm is a glycosaminoglycan derivative having fucose-substituted side chains. It has a chondroitin sulfate-like main chain composed of glucuronic acid (GlcUA) and acetyl galactosamine (GalNAc), and has fucose (L-fuc) side chains that are attached to the glucuronosyls of the main chain via α-1,3 glycosidic bonds. Both the hydroxyl groups of polysaccharides on the main chains and the side chains have different degrees of sulfation (*J. Biol. Chem.*, 1996, 271: 23973-23984; *Mar. Drugs*, 2013, 11: 399-417). Native FGAG has strong anticoagulant activity (*Thromb. Haemost.*, 2008, 100: 420-428; *J. Biol. Chem.*, 1996, 271: 23973-23984).

However, native FGAG still has extensive and contradictory pharmacological effects, including induction of platelet aggregation, bleeding tendency and activation of factor XII, etc (*Thromb. Haemost.*, 1988, 59: 432-434; *Thromb. Haemost.*, 1997, 65 (4): 369-373; *Thromb. Haemost.*, 2010, 103: 994-1004). Depolymerized FGAG after appropriate depolymerization may retain the anticoagulant activity of native FGAG and reduce the platelet activating activity (*Thromb. Haemost.*, 1991, 65: 369-373). China patents CN101724086B and CN101735336B disclose a method for preparing depolymerized FGAG, in which depolymerized FGAG is obtained by hydrogen peroxide depolymerization of FGAG, and the resultant products significantly decrease the bleeding tendency.

Since FGAG is a glycosaminoglycan derivative with large molecular weight and complex structure, on the premise of reducing the side effects while retaining the pharmacological activities, it is very difficult in technique to achieve depolymerization that can be effectively controlled in process to obtain a low molecular weight derivative with a characteristic terminal structure. Considering that the hydrogen peroxide depolymerization method lacks of selectivity toward glycosidic bond and the process control is complex, the present invention establishes a new method for depolymerization of FGAG—deacetylation deaminative depolymerization method. In this method, FGAG is first treated with hydrazine to subject D-2-(N-acetyl)amino-2-deoxygalactose (D-GalNAc) to partial deacetylation, to obtain partially deacetylated products of FGAG containing D-2-amino-2-deoxygalactosyl (D-GalNH$_2$); followed by treatment with nitrous acid and subjected to deaminative depolymerization to obtain depolymerized products of FGAG containing terminal 2,5-anhydrated talose or its reduced derivatives. In the prior art, FGAG depolymerization method by deacetylation and deamination has not been reported, and low-molecular-weight fucosylated glycosaminoglycan containing a terminal 2,5-anhydrated talose or its reduced derivatives has not been reported either.

SUMMARY OF THE INVENTION

Aiming at the problems existing in the prior art, it is an object of the present invention to provide a low-molecular-weight fucosylated glycosaminoglycan derivative and a pharmaceutically acceptable salt thereof. Said low-molecular-weight fucosylated glycosaminoglycan derivative is a low-molecular-weight fucosylated glycosaminoglycan having terminal 2,5-anhydrated talose (aTFG) or its reduced derivatives. Preparation method thereof, pharmaceutical compositions containing the aTFG, and use thereof for preventing and/or treating cardiovascular and cerebrovascular diseases are also provided.

In order to achieve the purposes of the present invention, the invention provides the following technical solutions:

A low-molecular-weight glycosaminoglycan derivative and its pharmaceutically acceptable salt, characterized in that the monosaccharide compositions of the low-molecular-weight glycosaminoglycan derivative comprise hexuronic acid, hexosamine, deoxyhexamethylose and 2,5-anhydrated talose or a reduced derivative thereof; wherein the hexuronic acid is D-β-glucuronic acid; the hexosamine is 2-N-acetamino-2-deoxy-D-β-galactose or 2-amino-2-deoxy-D-β-galactose or -β-D-2-sulfated amino-2-deoxygalactose; the deoxyhexamethylose is L-α-fucose; the reduced derivative of 2,5-anhydrated talose is 2,5-anhydrated talitol, 2,5-anhydrated talosamine or N-substituted -2,5-anhydrated talosamine.

based on molar ratio, the ratio of the monosaccharide compositions of the low-molecular-weight glycosaminoglycan derivative is hexuronic acid:hexosamine:deoxyhexamethylose=1:(1±0.35):(1±0.3); based on molar ratio, the ratio of 2,5-anhydrated talose and/or the reduced derivative thereof is not less than 3.0% of the total monosaccharide compositions.

The aTFG of the present invention has a weight average molecular weight (Mw) ranging from 2,500 Daltons to 20,000 Daltons;

The aTFG of the present invention has a polydispersity index (Mn/Mw) of between 1.0 and 1.8.

The aTFG of the present invention is a mixture of the homologous glycosaminoglycan derivatives having a structure of Formula (I),

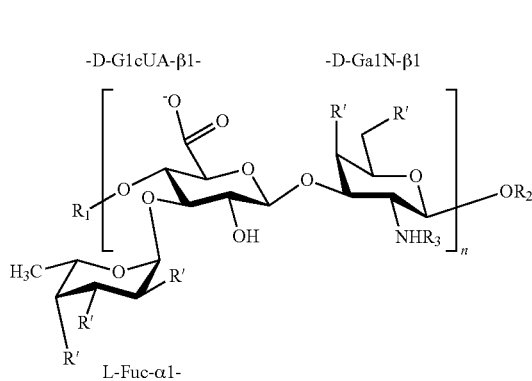

in Formula (I):

n is an integer with an average value of 3-21;

-D-GlcUA-β1- is -β-D-glucuronic acid-1-yl;

-D-GalN-β1- is -β-D-2-acetylamino-2-deoxygalactose-1-yl or -β-D-2-amino-2-deoxygalactose or -β-D-2-sulfated amino-2-deoxygalactose;

L-Fuc-α1- is α-L-fucose-1-yl;

R' is —OH or —OSO$_3^-$;

R$_3$ is —H, —SO$_3^-$ or acetyl;

R$_1$ is —H or β-D-2-acetylamino-2-deoxygalactose sulfate-1-yl;

R$_2$ is —H or -β-D-glucuronic acid-1-yl, or a group shown in Formula (II):

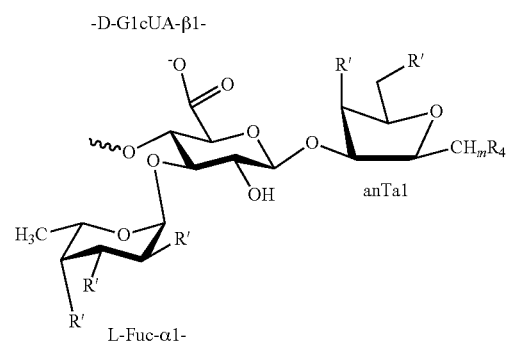

in Formula (II), -D-GlcUA-β1-, L-Fuc-α1-, and R' are defined as above;

anTal is 2,5-anhydrated talose, the alditol thereof, glycosylamine thereof or N-substituted glycosylamine thereof;

m is 1 or 2;

R$_4$ is optionally =O, —O, —NH$_2$, —NHR$_5$, wherein R$_5$ is C1-C6 straight chain or branched alkyl groups, C7-C12 aryl;

and, in the mixture of homologous glycosaminoglycan derivatives of Formula (I), based on molar ratio, the ratio of the compound that R2 is Formula (II) group to the compound that R$_2$ is —H or -β-D-glucuronic acid-1-yl is not less than 2:1.

The molecular weight of the aTFG of the present invention can be determined by high performance gel permeation chromatography (HPGPC). Based on weight average molecular weight, the aTFG selected by the present invention has a molecular weight ranging between 2,500 and 20,000 Daltons, that is, n of the homologues shown in Formula (I) has an average value of about 3-21. The preferred molecular weight range is between 5,000 and 12,000 Daltons, that is, n of the homologues shown in Formula (I) has an average value of about 5-15.

The aTFG of the present invention generally has a polydispersity index (PDI, ratio of weight average molecular weight to number average molecular weight, Mw/Mn) of between 1.0 and 1.8; preferably, the aTFG has a PDI of between 1.1 and 1.5.

The aTFG of the present invention may be a pharmaceutically acceptable salt form such as an alkali metal salt or an alkaline-earth metal salt; similarly, the aTFG may be an ester form that is formed with an organic alkaline group.

The pharmaceutically acceptable salt of the aTFG of the present invention is preferably sodium salt, potassium salt or calcium salt of the aTFG.

The aTFG of the present invention is a deaminative depolymerization product of fucosylated glycosaminoglycan from body wall and/or viscera of an echinoderm of the class Holothuroidea, or a derivative of the depolymerization product with reduction at the reducing terminal, thus it is another object of the present invention to provide a method for preparing the aTFG using FGAG as a raw material, the preparation method of the aTFG comprises the following steps of:

Step 1: treating fucosylated glycosaminoglycan (FGAG) from an echinoderm with hydrazine, subjecting the hexosamines (GalNAc) therein to partial deacetylation reaction, to obtain a partially deacetylated products of the FGAG; optionally, subjecting the obtained deacetylated products to sulfonation reaction to allow free amino groups to be sulfonated to obtain a sulfated amino derivative;

Step 2: treating the partially deacetylated products of the FGAG obtained in Step 1 with nitrous acid, subjecting it to deamination depolymerizative reaction, to obtain a low-molecular-weight fucosylated glycosaminoglycan with 2,5-anhydrated talosyl as a reducing terminal; optionally, subjecting the obtained low-molecular-weight fucosylated glycosaminoglycan to reduction reaction at the reducing terminal, comprising reducing 2,5-anhydrated talosyl terminal to an alditol, glycosylamine or N-substituted glycosylamine; the low-molecular-weight fucosylated glycosaminoglycan having a terminal 2,5-anhydrated talosyl or the alditol thereof, glycosylamine thereof or N-substituted glycosylamine thereof is the aTFG described in the present invention.

In the preparation method of the aTFG of the present invention, wherein the method of deacetylation reaction treated with hydrazine in Step 1 comprises: adding the fucosylated glycosaminoglycan from an echinoderm into anhydrous hydrazine or hydrazine hydrate solution, reacting at the temperature of 75° C.-125° C. for 2-14 h under stirring in the presence or absence of a catalyst.

Preferably, the deacetylation reaction in Step 1 is carried out in the presence of a catalyst. The catalyst may be selected from hydrazine sulfate, hydrazine hydrochloride and the like. In addition, a small amount of strong acid such as sulfuric acid and/or hydrochloric acid may be added into the reactive solvent as a catalyst. The added sulfuric acid and/or hydrochloric acid can react with the solvent hydrazine or hydrazine hydrate to produce hydrazine sulfate and/or hydrazine hydrochloride, which act as a catalyst. In a preferred embodiment of the present invention, the catalyst in the reaction solution has a concentration of 0.5%-2.5%.

After completion of the reaction of Step 1, the reaction solution can be evaporated under reduced pressure, or can be treated with alcohol precipitation, such as adding an equal volume of 80% ethanol, to precipitate the obtained products. During the alcohol precipitation, proper amount of sodium chloride solution can be added to precipitate more completely. The obtained partially deacetylated product of FGAG can be directly dried and used for the deaminative depolymerization of Step 2, or can be oxidized with iodic acid to remove excess hydrazine and hydrazine derivatives, followed by purification using suitable methods, and then dried and used for the deamination depolymerization of Step 2.

The partially deacetylated product of FGAG obtained in Step 1) can be detected by nuclear magnetic spectroscopy (NMR) to determine the deacetylation degree. Specifically speaking, deacetylation degree refers to ratio of methyl proton peak integrals of D-GalNAc and L-Fuc of the raw material to that of the product. Deacetylation degree of the reaction product can be calculated by the integral ratio of the methyl peaks.

Since the deaminative-depolymerization of Step 2 is a rapid and stoichiometric reaction, the deacetylation degree of the partially deacetylated product of FGAG obtained in Step 1) may determine the molecular weight of the final product aTFG from deaminative depolymerization. The inventors found that when the deacetylation degree of the partially deacetylated product of FGAG is about 5%-35%, the final product aTFG from deaminative depolymerization may have a molecular weight of about 4,000 to 20,000 Daltons.

In Step 2 of the method for preparing the aTFG of the present invention, the deaminative depolymerization treated with nitrous acid generally comprises the steps of: in ice bath or at room temperature, treating the partially deacetylated product of the FGAG obtained in Step 1 with 4-6 mol/L nitrous acid solution at pH 1.5-4.5 for 5-60 minutes, and adding an alkaline solution such as NaOH to adjust pH to 8 or above to terminate the reaction; and then optionally comprises:

(1) adding 3-5 volumes of ethanol into the reaction solution, standing still, centrifuging to obtain precipitation, purifying the obtained product through ultrafiltration or chromatography;

(2) reducing 2,5-anhydrotalose (anTal), the reducing terminal of the reaction product, into an alditol (anTalOH) by sodium borohydride or sodium cyanoborohydride, and then purifying the obtained product according to the procedure of Step (1);

(3) reducing 2,5-anhydrotalose, the reducing terminal of the reaction product, into a glycosylamine or N-substituted glycosylamine through reductive amination, and then purifying the obtained product according to the procedure of Step (1).

The terminal reduction reaction of Step 2(2) generally comprises the following steps of: after adjusting pH 8-9 with NaOH to terminate the deaminative-depolymerization reaction, adding sodium borohydride and/or sodium cyanoborohydride until reaching a concentration of 0.05-0.5 mol/L, stirring at 50° C. for 20-60 minutes to allow anTal to be fully transformed into anTalOH. After cooling the reaction solution to room temperature, adding an acid to adjust pH to 3-4 to remove excess borohydride and/or sodium cyanoborohydride, followed by neutralizing with an alkaline solution such as NaOH, and then purifying the obtained products according to the procedure of Step (1).

Step 2(3) comprises subjecting the terminal anTal to reductive amination reaction in the presence of ammonium bicarbonate or organic amine and an reducing agent, namely reacting ammonium salt or organic amine with the aldehyde groups of anTal to produce a Schiff base, which is reduced into a secondary amine in the presence of a reducing agent such as sodium cyanoborohydride.

The obtained aTFG product of the present invention can be detected by NMR. Generally, it is calculated according to the NMR spectrum. Based on the molar ratio, in the aTFG product of the present invention, the compound having terminal 2,5-anhydrated talose or its reduced derivatives may account for 60%-97% of the total depolymerized products.

The reaction route of D-GalNAc deacetylation, D-GalNAc deamination and anTal carbonyl reduction and reductive amination in the method of the present invention is shown in the "reaction route". In this route, R', $R_5$ in compounds (1)-(5) are defined as above. For the ordinary person skilled in the art, in the reductive amination reaction, when $R_5$ is H, C1-C6 linear or branched alkyl or C7-C12 aryl, the final products of reaction, compounds (5) shown in the route, can be easily obtained.

(Reaction route)

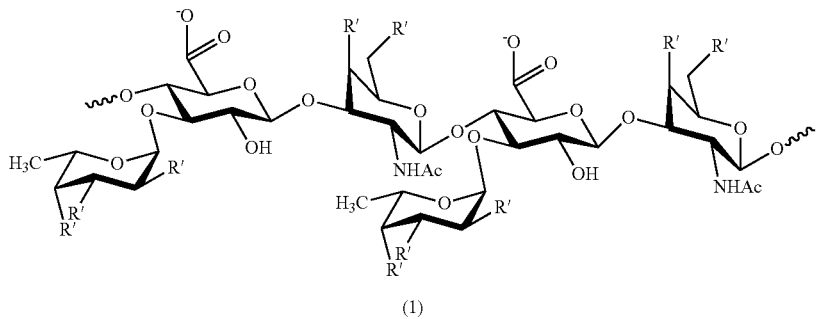

(1)

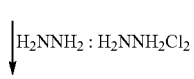

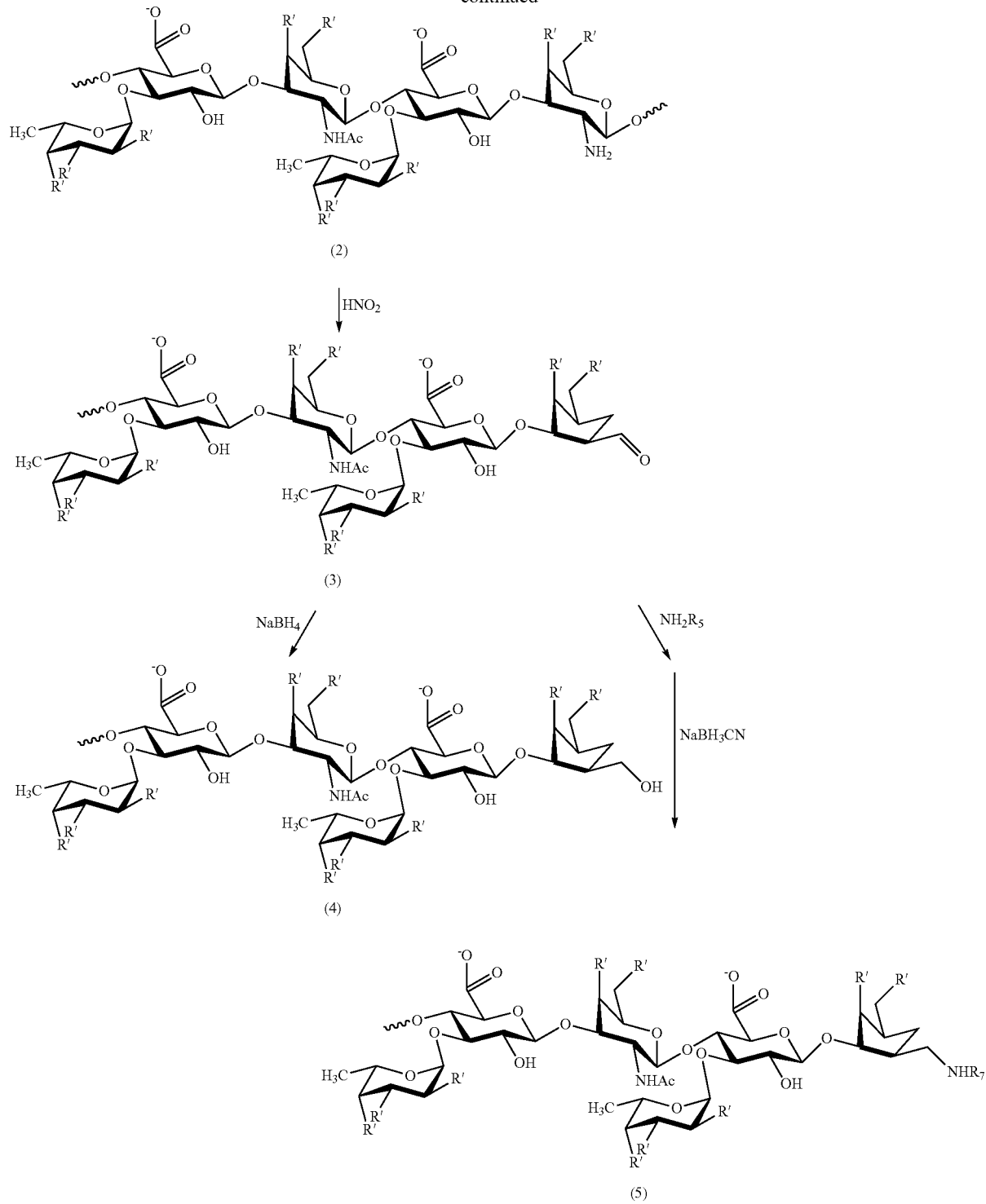

Native FGAG has complex main chain and side chain structure, the effective implementation of the selective deacetylation reaction is a key technical difficulty. The side chain L-Fuc is prone to acid hydrolysis so that the control of deaminative-depolymerization reaction conditions with $HNO_2$ is particularly important. The technical route and its main technical parameters of the present invention can ensure the smooth operation of these reactions.

In the method of the present invention, the aTFG final product can be purified by the known method in the prior art (CN 101735336A). For example, dialysis or ultrafiltration can be used for removal of impurities such as small molecules salt, or gel filtration or DEAE ion exchange chromatography can be used for further purification, etc.

In the method of the present invention, during the removal of impurities by dialysis, according to the molecular weight size of target compounds, dialysis membrane and ultrafiltration membrane bag with appropriate molecular weight cutoff can be selected, preferably dialysis membrane and ultrafiltration membrane bag with molecular weight cutoff 1,000 Daltons is used to remove small molecules. Dialysis time should be determined according to the specific process conditions, usually not less than 6 hours. Dialysis can also be selected for removal of other macromolecular impurities and undepolymerized FGAG or aTFG beyond the desirable molecular weight range.

The final product aTFG obtained according to the method of the present invention can be prepared into a single salt form by cation exchange, such as sodium salt, potassium salt or calcium salt. The salt formation process of the aTFG product may comprise: transforming the aTFG into the hydrogen type by ion exchange, followed by neutralizing with an alkali to obtain the corresponding salt of aTFG; or preferably directly exchanging the aTFG to form a salt on the column by dynamic ion exchange method. Resin column pretreatment, sample loading and elution can be carried out according to conventional methods.

In the preparation method of aTFG of the present invention, the starting material of "Step 1" is fucosylated glycosaminoglycan (FGAG) from an echinoderm. Said FGAG has a chondroitin sulfate-like main chain. Generally, the main chain is composed of glucuronic acid (D-GlcUA) and 2-(N-acetyl) amino-2-deoxygalactose (D-GalNAc), and the monosaccharide compositions are sequentially connected by glycosidic bonds, -4)-D-GlcUA-($\beta$-1- and -3)-D-GalNAc-($\beta$-1-, respectively. FGAG also has fucose (L-Fuc) side chains. Generally, the L-Fuc side chain is linked to D-GlcUA of the main chain via $\alpha$-1,3 glycosidic bond. In addition, hydroxyl groups of both D-GalNAc in the main chains and in the L-Fuc side chains may have different degrees of sulfation J. Biol. Chem., 1996, 271: 23973-23984; Mar. Drugs, 2013, 11: 399-417).

FGAG for preparing the aTFG and its pharmaceutically acceptable salt of the present invention may be from a sea cucumber selected from the groups consisting of, but not limited to, Stichopus variegates Semper, Holothuria scabra Jaeger, Holothuria leucospilota Brandt, Holothuria edulis Lesson, Bohadschia argus Jaeger, Stichopus chloronotus Brandt, Holothuria sinica Liao, Thelenota ananas Jaeger, Acaudina molpadioides Semper, Pearsonothuria graeffei Semper and Holothuria nobilis Selenka. With regard to other species of sea cucumber from different regions in the world, as long as FGAG from which consists with the above structure characteristic, it can be subjected to the deaminative-depolymerization method of the present invention, to obtain the desirable final product. Therefore, the method of the present invention is not restricted by the specific species of sea cucumbers.

The studies of the invention showed that different sea cucumber species, different tissue sources and even different extraction methods may produce FGAG having different monosaccharide compositions, side chain types and sulfation degrees. The ordinary person skilled in the art can easily understand that since these differences do not involve the structure characteristic of acetyl amino groups in the FGAG, they do not affect the implementation and application of the deaminative depolymerization method of the present invention.

The studies of the invention showed that said aTFG has potent anticoagulant activity, and its drug concentration that is required for doubling the activated partial thromboplastin time (APTT) of human control plasma is not more than 12 µg/mL. The studies also confirmed that the aTFG have a potent activity of inhibiting intrinsic tenase complex (f.Xase). The $EC_{50}$ for inhibition of f.Xase is about 5-50 ng/mL. Since factor Xase is the last enzymatic site in the intrinsic coagulation pathway, and is the rate limiting site of the coagulation process induced by many factors, such inhibitor may have significant anti-thrombotic activity while have little influence on physiological hemostasis (Blood, 2010, 116(22), 4390-4391; Blood, 2009, 114, 3092-3100).

The aTFG and its pharmaceutical acceptable salts have definite anticoagulant activity and thus have a clear potential value for medicinal use. The aTFG has good water solubility; therefore, it can be easily prepared into a solution preparation or freeze-dried products. As a polysaccharide component, its oral bioavailability is limited, so its pharmaceutical composition is preferably prepared into a parenteral dosage form and the preparation may be prepared according to the well-known technical methods in the prior art.

Therefore, the invention also provides a pharmaceutical composition containing an effectively anticoagulant amount of the low molecular weight glycosaminoglycan derivative or a pharmaceutically acceptable salt thereof, and pharmaceutically acceptable excipients. The dosage form of the pharmaceutical composition can be water soluble for injection or freeze-dried powder for injection.

The aTFG of the invention has a potent anticoagulant activity, and thus can be used for the prevention and treatment of different thrombotic diseases, such as thrombotic cardiovascular disease, thrombotic cerebrovascular disease, pulmonary venous thrombosis, peripheral venous thrombosis, deep venous thrombosis, and peripheral arterial thrombosis and so on. Therefore, the invention also provides a use of the low molecular weight glycosaminoglycan derivative (aTFG) or its pharmaceutically acceptable salt and the pharmaceutical composition containing the low molecular weight glycosaminoglycan derivative (aTFG) or its pharmaceutically acceptable salt for preparing medicines for the prevention and/or treatment of thrombotic disease. The thrombotic diseases can be referred to venous thrombosis or arterial thrombosis or ischemic heart disease and ischemic cerebrovascular disease.

Compared with the prior art, the invention has the following advantages:

At present, the reported FGAG depolymerization method is mainly FGAG depolymerization by hydrogen peroxide. The depolymerization method lacks of selectivity toward specific glycosidic bonds and the process control is complex. The present invention establishes a new FGAG depolymerization method: deacetylation-deaminative-depolymerization method. The method firstly subjects the D-2 (N-acetyl)amino-2-deoxygalactose (D-GalNAc) in FGAG to partial deacetylation reaction by hydrazinolysis deacetylation, to obtain partially deacetylated product containing D-2-amino-2-deoxygalactosyl (D-GalNH$_2$) of FGAG; then subjects to deaminative depolymerization by nitrous acid treatment, to obtain the depolymerized products containing terminal 2,5-anhydrated talose or its reduction derivatives of FGAG. The person skilled in the art can easily understand that the complex chemical structure of FGAG, particularly the existing of large number of fucose (Fuc) side chain substituents, makes the selective removal of amino groups in GalNAc of FGAG have obvious technical difficulties; and the Fuc side chain can be easily cleaved under acidic conditions, therefore, technical challenge also exists when partially deacetylated FGAG is subjected to deamination under acidic conditions. The present invention first discloses the deaminative depolymerization method of FGAG with complex structure to obtain derivatives having characteristic terminal structure, and first discloses a FGAG depolymerized product having terminal 2,5-anhydrated talose or its reduction derivatives.

The advantages of the method and the obtained products of the invention are: (1) the deacetylation deaminative depolymerization of FGAG has selectivity toward specific glycosidic bonds, i.e., selectively cleaves D-GalNH$_2$ (β1-) glycosidic bonds, but not cleave L-Fuc(α1-) and D-GlcUA (β1-) glycosidic bonds, thus the obtained depolymerized product has better structural homogeneity; (2) the product of FGAG by deacetylation deaminative depolymerization has terminal 2,5-anhydrated talose (anTal) or its reductive derivatives. The characteristic terminal is in favor of the chemical structure analysis and quality control of the depolymerized products, and the reduction derivatization treatment of the terminal can allow it to be effectively used for analysis of pharmacokinetics and pharmacology mechanism; (3) partially deacetylated FGAG can be treated with HNO$_2$ to perform stoichiometric deaminative depolymerization. Therefore, by controlling of the deacetylation degree, the molecular weight range of the depolymerized product can be better controlled, and the controllability of the preparation process of the FGAG depolymerized products can be effectively improved.

DETAILED DESCRIPTION OF THE INVENTION

Figure 1:
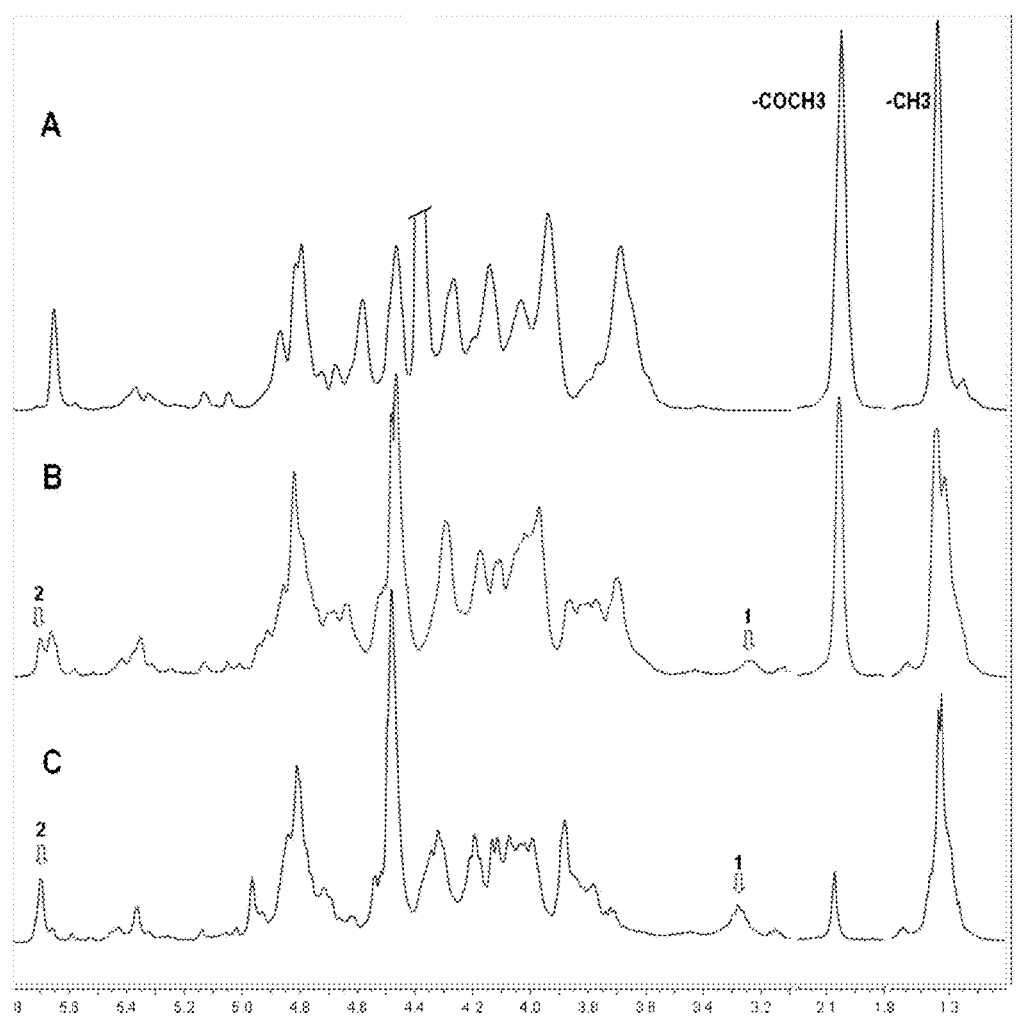
FIG. 1 is $^1$H NMR spectra of FGAG and its deacetylated products, dAFG-1 and dAFG-2.

The following examples are provided to illustrate the present invention in detail, but not intended to limit the scope of the invention.

Example 1

Preparation of the Deacetylated Product of FGAG (dAFG)

1.1 Materials

FGAG: fucosylated glycosaminoglycan from the body wall of *Thelenota ananas* was prepared according to purification method disclosed in the reference (Marine Drugs, 2013, 11, 399-417), with a molecular weight of 69,930 Daltons. Hydrazine hydrate, hydrazine sulfate, hydrazine hydrochloride, hydrochloric acid, sodium chloride, anhydrous alcohol, iodic acid, hydriodic acid, sodium hydroxide and other reagents were commercially available analytical reagents.

1.2 Methods

Deacetylation Reaction:

60 mg of raw material FGAG was weighed accurately and placed in a reaction tube. Optionally, 14.5 mg of hydrazine sulfate or 12.2 mg of hydrazine hydrochloride or 0.1 mL of 2.304 mol/L HCl was added as catalyst, or not added. Then 1.45 mL of hydrazine hydrate or anhydrous hydrazine was added. Under nitrogen atmosphere, the mixture was reacted at 75-105° C. for 2 to 14 hours while stirring at 250 rpm. After completion of the reaction, the reaction solution was precipitated with 80% ethanol, centrifuged to obtain precipitation, which was dried under vacuum to obtain deacetylated intermediate product sample. The sample can be directly used for nitrous acid depolymerization, or further treated to obtain relatively pure intermediate, wherein the treatment method was: the sample was evaporated and cooled in ice bath, added dropwise with 0.25 mol/L iodic acid solution until the precipitation was not dissolved and appeared to be black suspension solution. About 5 mL of 45% hydriodic acid was dropwise added, and then 3 mol/L NaOH was added to dissolve the precipitation, until the solution became clear and transparent or light yellow solution. The solution was adjusted to neutral pH, and dialyzed using a dialysis bag with 1,000 Daltons molecular weight cutoff, and freeze-dried.

Determination of the Degree of Deacetylation:

About 5 mg of the above deacetylated product was accurately weighed and dissolved in about 600 ml deuteroxide (TSP-containing internal standard). BUCKER DRX-500 nuclear magnetic resonance spectrometer was used to determine the sample. Degree of deacetylation (DD) was calculated by the ratio of integral area of the two methyl protons in $^1$H NMR spectra (methyl of acetyl amino groups in acetyl galactosamines and methyl in sulfated fucose side chains).

Determination of Molecular Weight of the Product:

The molecular weight of the product was determined by high performance gel permeation chromatography (HPGPC). Agilent technologies 1200 series high performance liquid chromatography, Shodex Ohpak SB-804 HQ (7.8 mm×300 mm) column, temperature: 35° C., detector: differential refractive index detector (G1362A). Proper sample was accurately weighed, dissolved in 0.1 mol/L sodium chloride solution, diluted to 10 mL in a 10 mL volumetric flask, mixed well, filtered through a 40 μm filter membrane. The filtrate was used as a sample solution.

Preparation of Standards and Reference Solution:

Series dextran standards with certain molecular weight were accurately weighed, dissolved and diluted with 0.1 mol/L sodium chloride solution to obtain 10 mg/mL solution, as narrow standard correction solution. FGAG control with known molecular weight was accurately weighed, dissolved and diluted with 0.1 mol/L sodium chloride solution to obtain 10 mg/mL solution. Each 25 μL of the sample, standard, control solutions was injected into the liquid chromatographic apparatus, and the chromatograms were recorded. The data were analyzed using the special GPC software.

Detection of Chemical Components:

The monosaccharide components acetyl galactosamine, glucuronic acid and fucose were determined by Elson-Morgon method, m-hydroxyldiphenyl method, and cysteine-phenol method, respectively (Zhang weijie, Biochemical Research Technology of Glycoconjugate 2Ed, Zhejiang: Zhejiang University Press, 1999). The molar ratio of sulfate groups to carboxyl groups was determined by conductometric method (Zhang weijie, Biochemical Research Technology of Glycoconjugate 2Ed, Zhejiang: Zhejiang University Press, 1999, 409-410).

1.3 Results

The effect of the different reaction conditions on deacetylation degree of the deacetylated product (deacetylated FGAG, dAFG) is shown in Table 1. The results showed that the addition of the catalyst can accelerate the reaction process, and the deacetylation degree of the deacetylated product is higher. Deacetylated product with different deacetylation degrees can be obtained by controlling reaction time, reaction temperature and mass concentration of hydrazine.

TABLE 1

Experimental results of the deacetylation reaction under different conditions

| Factor | | Methyl integral of acetylamino groups | Methyl integral of fucose side chains | Deacetylation degree (DD) |
|---|---|---|---|---|
| Reaction time | 2 h | 1 | 0.92 | 0.065 |
| | 6 h | 1 | 1.03 | 0.167 |
| | 10 h | 1 | 1.23 | 0.301 |
| | 14 h | 1 | 1.31 | 0.342 |
| | 24 h | 1 | 1.79 | 0.519 |
| | 36 h | 1 | 2.79 | 0.691 |
| | 48 h | 1 | 3.98 | 0.784 |
| Catalyst | no catalyst | 1 | 0.98 | 0.123 |
| | hydrazine sulfate | 1 | 1.25 | 0.310 |
| | hydrazine hydrochloride | 1 | 1.28 | 0.330 |
| | hydrochloride acid | 1 | 1.24 | 0.306 |
| Reaction temperature | 60° C. | 1 | 0.88 | 0.010 |
| | 75° C. | 1 | 1.00 | 0.134 |
| | 90° C. | 1 | 1.26 | 0.319 |
| | 105° C. | 1 | 2.08 | 0.582 |
| Hydrazine concentration | 32% | 1 | 0.94 | 0.084 |
| | 64% | 1 | 1.26 | 0.315 |
| | 100% | 1 | 3.04 | 0.704 |

Figure 2:
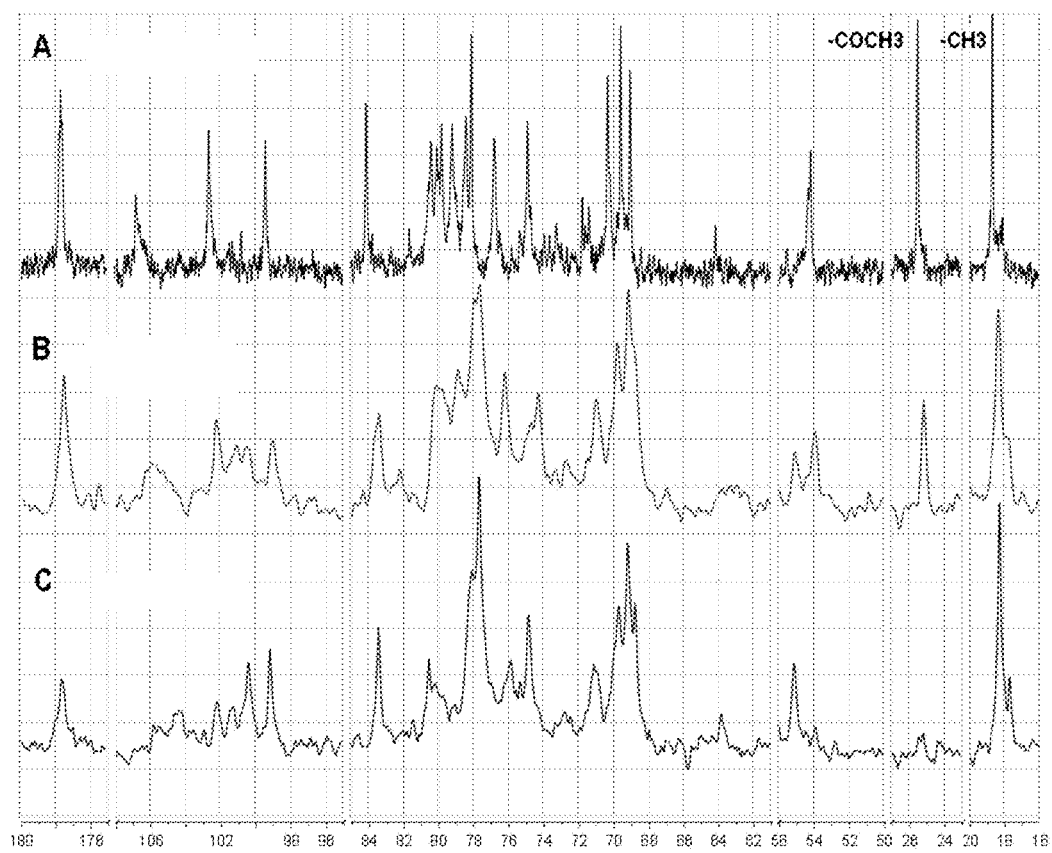
FIG. 2 is $^{13}$C NMR spectra of FGAG and its deacetylated products, dAFG-1 and dAFG-2.
Figure 3:
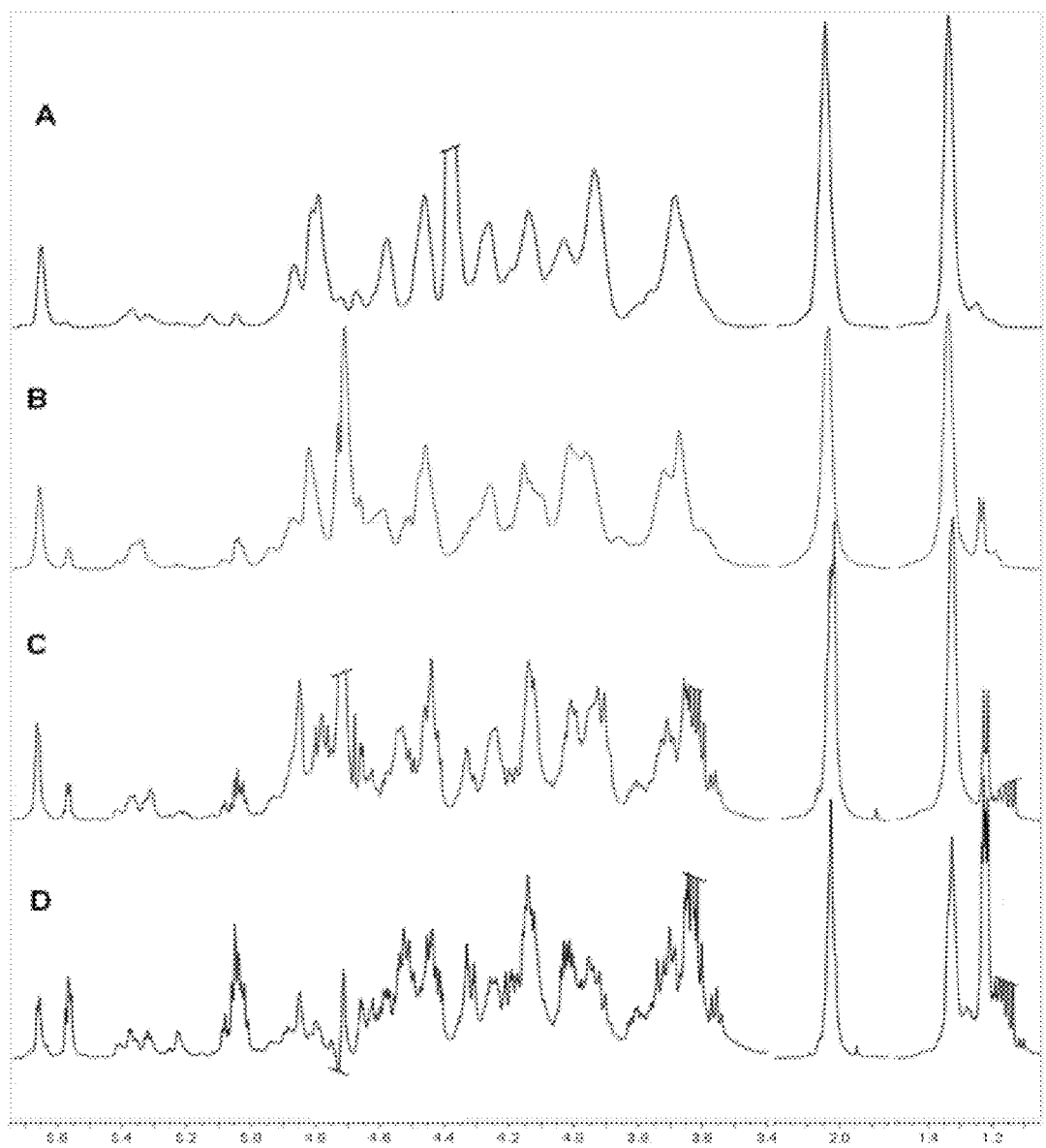
FIG. 3 is $^1$H NMR spectra of FGAG and its deacetylated deaminative depolymerization products aTFG-a, aTFG-b and aTFG-c.
Figure 4:
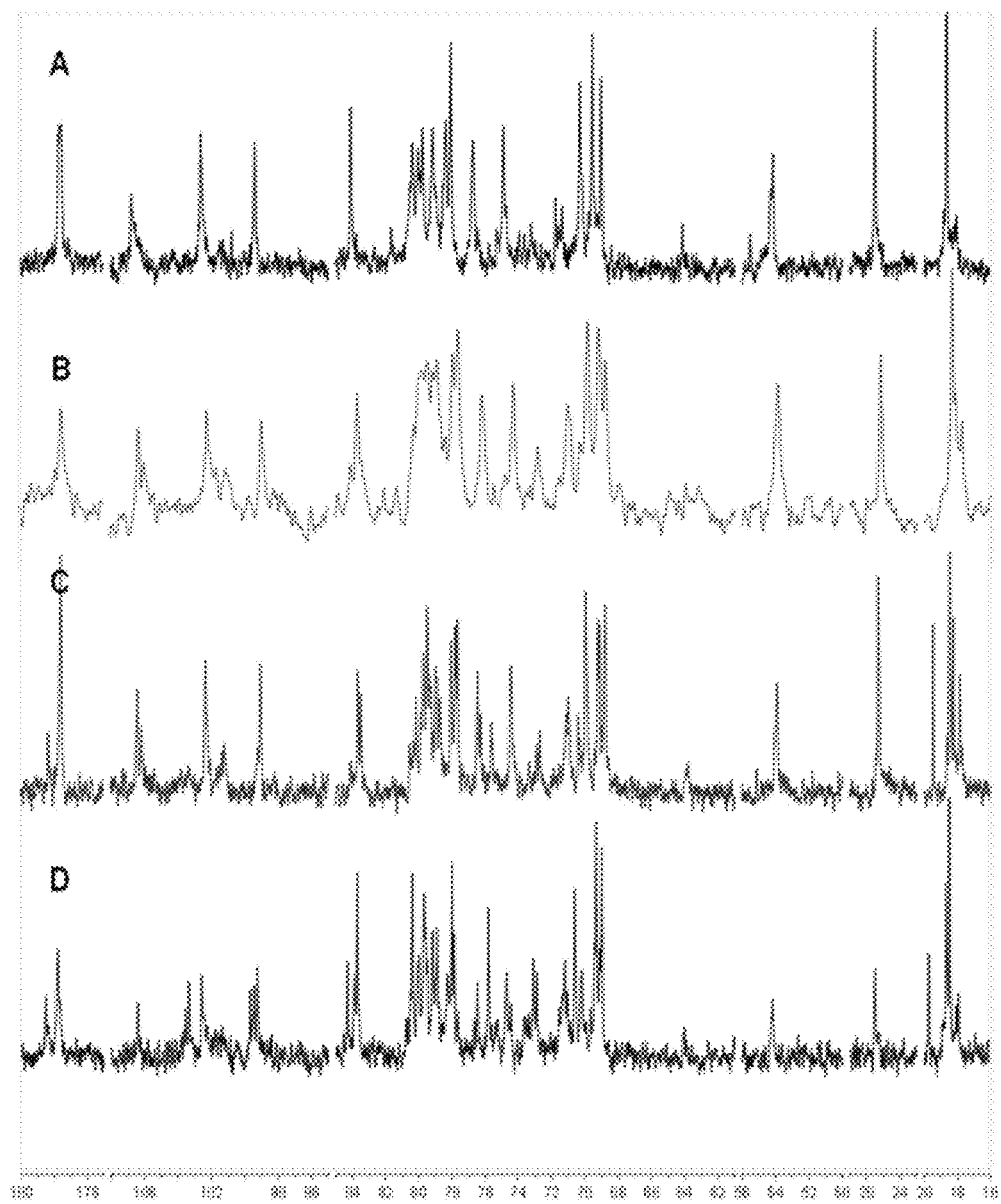
FIG. 4 is $^{13}$C NMR spectra of FGAG and its deacetylated deaminative depolymerization products aTFG-a, aTFG-b and aTFG-c.
Figure 5:
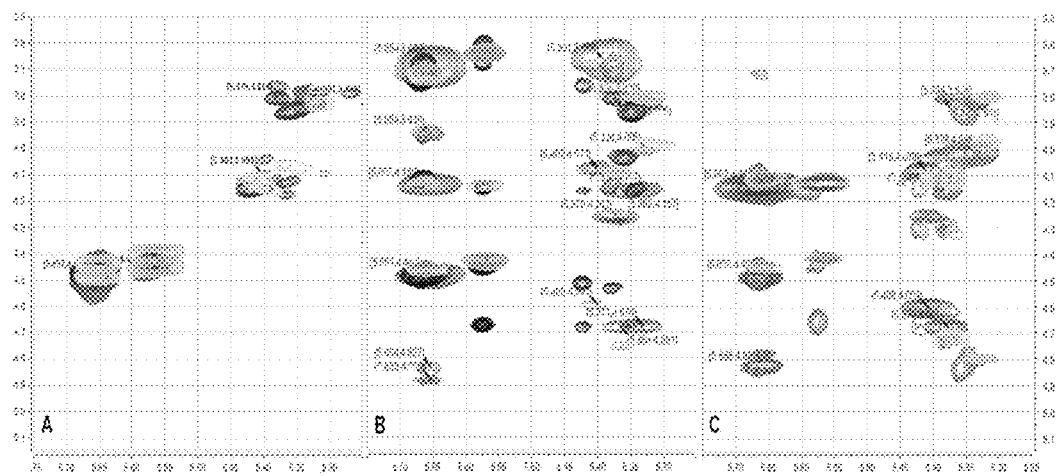
FIG. 5 is spectral overlay (partial) diagram of COSY (A), NOESY (B), TOCSY (C) of FGAG and its deacetylated deaminative depolymerization products aTFG-a, aTFG-b.
Figure 6:
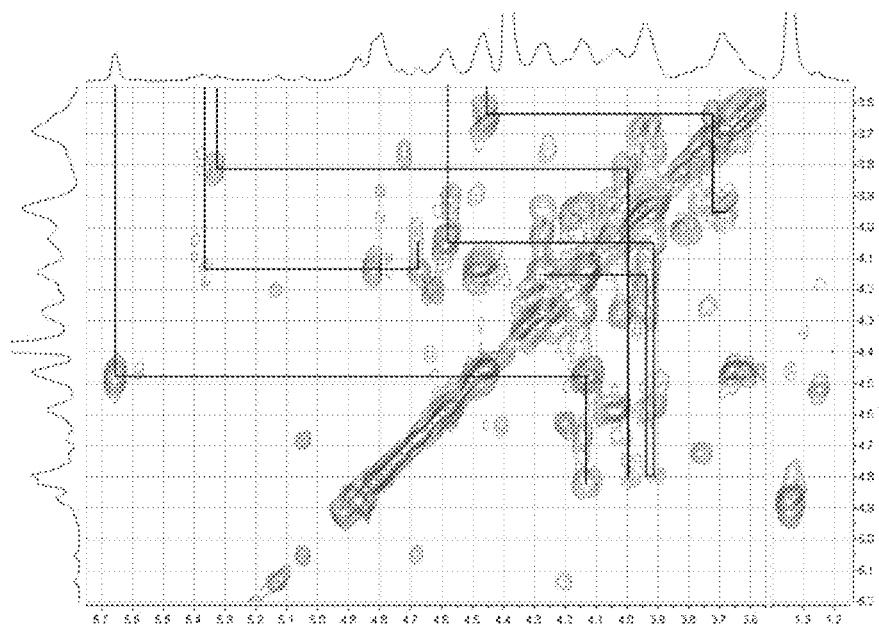
FIG. 6 is $^1$H COSY spectra of FGAG (A) and its deacetylated deaminative depolymerization product aTFG-b (B).
Figure 6:
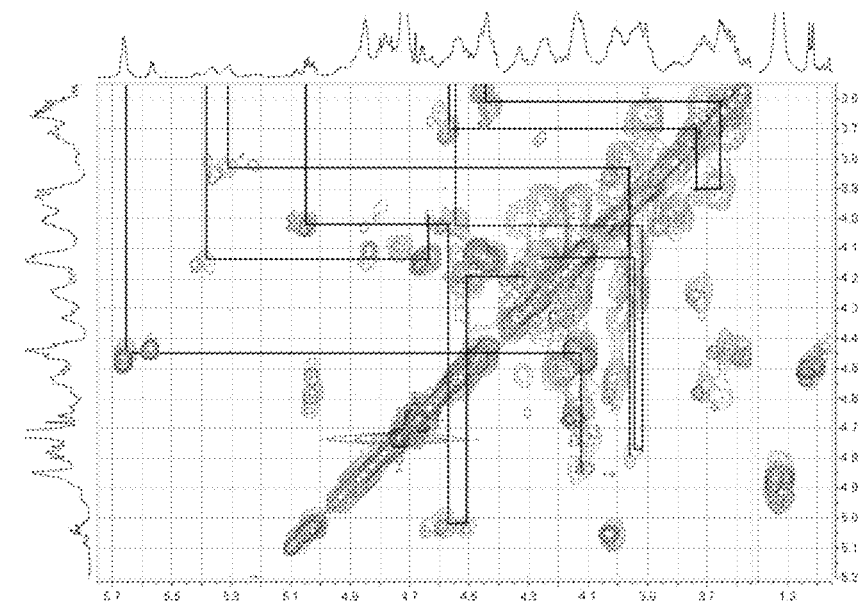

FIGS. 1 and 2 showed the $^1$H, $^{13}$C-NMR spectra of two samples prepared according to the method of this example, dAFG-1 and dAFG-2, which had different deacetylation degrees. Their deacetylation degrees were calculated based on the spectra to be 48% and 88%, respectively. The spectra data also showed that before and after deacetylation, except that partial D-GalNAc was deacetylated to produce D-GalNH$_2$, there was no significant change in the basic structure. By analysis of monosaccharide compositions before and after deacetylation, the molar ratio of the monosaccharide compositions, (D-GlcUA):(D-GalNAc+D-GalNH$_2$):(L-Fuc), is about 1:(1±0.3):(1±0.3). This result further suggested that except that D-GalNAc was partially deacetylated, the basic structure of the polysaccharide remained s stable.

Example 2

Preparation of aTFG by Deaminative Depolymerization of dAFG 2.1 Materials dAFG, namely partially deacetylated product of FGAG, prepared according to the method of Example 1; Reagents such as sodium nitrite, concentrated sulfuric acid, sodium borohydride, sodium carbonate, sodium hydroxide, anhydrous alcohol were commercially available analytical pure reagents.

2.2 Methods

Preparation of Products:

About 20 mg of deacetylated intermediate products was accurately weighed and placed in a reactor, dissolved in 1 mL of water; in ice bath or at room temperature, added with 2 mL of 5.5 mol/L nitrous acid solution (pH 4), and depolymerized for 2 to 30 minutes. After completion of the reaction, 1 mol/L sodium carbonate solution was added to adjust pH to 8-9 to terminate the reaction. 1 mL of 0.1 mol/L sodium hydroxide containing 0.25 mol/L sodium borohydride was added to reduce aldehyde groups of the product depolymerized with nitrite acid, heated at 50° C. for 40 minutes. After completion of the reaction, the reaction solution was cooled to room temperature, and added with 0.5 mol/L sulfuric acid to remove excess sodium borohydride, neutralized with 0.5 mol/L sodium hydroxide solution, and dialyzed with a 1,000 Daltons dialysis bag. The dialysis fluid in the dialysis bag was collected and lyophilized.

Determination of Product:

The depolymerized product was determined by BUCKER DRX-500 nuclear magnetic resonance spectrometer. The molecular weight of the depolymerized sample was determined by gel exclusion chromatography. The molar ratio of sulfate groups to carboxyl groups of the depolymerized sample was determined by conductivity method.

2.3 Results

The yield of final deaminative depolymerization product was more than 90%, and the purity of the sample was more than 95%.

Theoretically, only free amino groups can be eliminated by nitrous acid to cleave glycosidic bonds. Therefore, according to the deacetylation degree of the sample before nitrous acid depolymerization, the number of free amino groups can be calculated and the possible molecular weight of the depolymerization products can further be calculated theoretically. The experiment results are shown in Table 2. The molecular weight of the products obtained from raw materials with different molecular weights by nitrous acid depolymerization was substantially identical to the theoretical calculated value. This indicated that based on the deacetylation degree, final depolymerized products with theoretically calculated molecular weight can be obtained.

TABLE 2

Experiment results of the relationship between deacetylation degree and molecular weight of products

| Molecular weight of starting material | Deacetylation degree | Theoretical molecular weight of product | Actual molecular weight of product |
|---|---|---|---|
| 13710 | 11.50% | 8245 | 8777 |
| 13710 | 13.79% | 6577 | 6751 |
| 64300 | 15.96% | 5680 | 7083 |
| 64300 | 8.26% | 10984 | 9702 |

The NMR spectra of the three products aTFG-a, aTFG-b and aTFG-c prepared by this example are shown in FIGS. 3 to 6. The NMR spectra of the raw materials FGAG and intermediate products dAFG were compared. According to $^1$H NMR, $^{13}$C NMR and $^1$H homonuclear related spectra COSY, TOCSY, NOESY and $^1$H—$^{13}$C heteronuclear related spectra HQSC, HMBC, the nitrous acid depolymerization products aTFG-a, aTFG-band and aTFG-c with different deacetylation degrees (15%, 48%, 88%) were subjected to signal assignment, and the NMR signal data are shown in Table 3.

and 1.1%, respectively. Their weight average molecular weights were from about 50,000 Daltons to 80,000 Daltons. $^1$H NMR spectra were used to determine the structure characteristic of AJG, HEG, LGG, HLG and HNG: ano-

TABLE 3

$^1$H/$^{13}$C NMR signal assignments of FGAG and its deaminative depolymerization product aTFG-b

| | H-1 | H-2 | H-3 | H-4 | H-5 | H-6 | Ac | C-1 | C-2 | C-3 | C-4 | C-5 | C-6 | Ac | |
|---|---|---|---|---|---|---|---|---|---|---|---|---|---|---|---|
| | | | | | | | —CH$_3$ | | | | | | | —CH$_3$ | C=O |
| | | | | | | | FGAG | | | | | | | | |
| β-GalNAc 4S6S | 4.58 | 4.05 | 3.92 | 4.79 | 3.94 | 4.16, 4.26 | 2.05 | 102.6 | 54.1 | 79.8 | 79.2 | 76.8 | 70.3 | 25.5 | 177.6 |
| β-GlcUA | 4.46 | 3.64 | 3.73 | 3.94 | 3.68 | / | / | 106.8 | 76.8 | 80.5 | 79.8 | 80.4 | 177.6 | / | / |
| α-Fuc2S4S | 5.66 | 4.48 | 4.14 | 4.83 | 4.88 | 1.34 | / | 99.4 | 78.0 | 69.6 | 84.1 | 69.0 | 18.6 | / | / |
| α-Fuc4S | 5.33 | 3.82 | 4.01 | 4.81 | 4.91 | 1.34 | / | 101.4 | 71.4 | 74.0 | 80.5 | 69.0 | 18.6 | / | / |
| α-Fuc3S | 5.37 | 4.15 | 4.69 | 4.03 | 4.52 | 1.25 | / | 101.2 | 71.8 | 83.9 | 73.3 | 69.3 | 18.6 | / | / |
| | | | | | | | aTFG | | | | | | | | |
| β-GalNAc 4S6S | 4.54 | 4.02 | 3.92 | 4.77 | 3.95 | 4.14, 4.24 | 2.02 | 102.3 | 51.8 | 78.1 | 79.0 | 74.4 | 67.7 | 23.2 | 177.6 |
| anTal4S6S | 5.05 | 4.02 | 4.58 | 5.02 | 4.50 | 4.19, 4.32 | / | 91.6 | 84.4 | 79.1 | 80.5 | 80.4 | 68.2 | / | / |
| β-GlcUA | 4.44 | 3.59 | 3.66 | 3.89 | 3.72 | / | / | 106.4 | 76.4 | 80.3 | 79.2 | 79.4 | 177.6 | / | / |
| α-Fuc2S4S | 5.66 | 4.45 | 4.13 | 4.85 | 4.89 | 1.33 | / | 99.0 | 77.8 | 70.1 | 83.6 | 68.8 | 18.5 | / | / |
| α-Fuc4S | 5.31 | 3.83 | 3.97 | 4.80 | 4.86 | 1.33 | / | 101.3 | 71.1 | 72.6 | 79.9 | 69.0 | 17.8 | / | / |
| α-Fuc3S | 5.38 | 4.13 | 4.63 | 4.02 | 4.50 | 1.22 | / | 101.2 | 72.8 | 83.5 | 71.3 | 68.8 | 18.2 | | |

As shown in Table 3 and FIGS. 3-6, the $^1$H NMR spectra of the deaminative depolymerization products aTFG of FGAG were substantially similar, but the signal of H-2 of D-β-acetyl galactosamine (D-β-GalNH$_2$) at about 3.1-3.2 ppm disappeared, which was present in deacetylated FGAG, indicating that the hexosamine having free amino groups have been reacted, but there was a new signal at about 5.0-5.1 ppm, which was from reductive terminal 2,5-anhydrated talose (anTal, terminal group and H-4). Compared with the deacetylated products, $^1$H NMR signal of the deaminative depolymerization products was closer to that of the native FGAG.

Example 3

Preparation of Nitrous Acid Depolymerization Products of FGAG from Different Sea Cucumbers 3.1 Materials

*Apostichopus japonicus, Holothuria edulis, Ludwigothurea grisea, Holothuria leucospilota, Holothuria nobilis,* were commercially available dry body wall.

3.2 Methods (1) Each dry body wall of *Apostichopus japonicus, Holothuria edulis, Ludwigothurea grisea, Holothuria leucospilota, Holothuria nobilis* was crushed. 300 g of each crushed material was extracted according to the method of Example 1(1) to obtain FGAG, designated as AJG, HEG, LGG, HLG and HNG, respectively.

(2) About 1 g of each AJG, HEG, LGG, HLG and HNG was weighed and used to prepare deaminative depolymerization products aTFG according to the method of Example 1 and 2, designated as aAJG, aHEG, aLGG, aHLG and aHNG respectively.

3.3 Results

The yields of AJG, HEG, LGG, HLG and HNG that were extracted and purified from *Apostichopus japonicus, Holothuria edulis, Ludwigothurea grisea, Holothuria leucospilota, Holothuria nobilis* were about 1.4%, 0.9%, 0.8% meric protons and other protons of α-L-Fuc, β-D-GalNAc and β-D-GlcUA were clearly determined.

The yields of aAJG (8,000 Daltons), aHEG (10,500 Daltons), aLGG (7,300 Daltons), HLG (10,200 Daltons) and aHNG (8,700 Daltons) prepared from AJG, HEG, LGG, HLG and HNG were about 40%-70% respectively. $^1$H NMR spectra were used to determine the related characteristic signals of anTal obtained by depolymerization.

Example 4

Preparation of Terminal Reductive Amination Products 4.1 Materials aTFG: prepared as described in Examples 1 and 2. Tyramine, sodium cyanoborohydride and other reagents were commercially available and analytical pure.

4.2 Methods (1) Terminal Reductive Amination:

About 0.1 g of the aTFG obtained in Example 2 was dissolved in 3.5 mL of 0.2 mM phosphate buffer (pH8.0), added with 80 mg of excess Tyramine and 30 mg of sodium cyanoborohydride under stirring, reacted in constant water bath at 35° C. for about 72 hours. At the end of the reaction, 10 mL of 95% ethanol was added, centrifuged to obtain precipitation. The obtained precipitation was washed twice with 30 mL of 95% ethanol, and then the precipitation was dissolved in 35 mL of 0.1% NaCl, centrifuged to remove insoluble matters. The supernatant was placed in 1,000 Daltons dialysis bag, dialyzed with deionized water for 24 hours, and lyophilized to obtain 82 mg dLFG-2A.

(2) Physicochemical and Spectral Detection of Products:

Molecular weight and distribution was determined by HPGPC. The —OSO$_3^-$/—COO$^-$ ratio was determined by conductivity method. The content of acetyl galactosamine (D-GalNAc) was determined by Elson-Morgon method. The content of glucuronic acid (D-GlcUA) was determined by carbazole method. D-GalNAc/L-Fuc molar ratio was calculated by $^1$H NMR methyl peak area (the same as Example 1).

NMR spectra were detected by AVANCE AV 500 superconducting nuclear magnetic resonance meter (500 MHz) (Bruker company, Switzerland).

4.3 Results

The yield of the products was about 72%, calculated based on the starting material. The determination results of the product compositions showed that D-GalNAc:D-GlcUA:L-Fuc:—$OSO_3^-$ was about 1.00:0.98:1.10:3.60, Mw was about 9,969 Daltons, and PDI was about 1.32.

$^1$HNMR ($D_2O$, δ [ppm]): 7.25 (2', 6'H); 6.83 (3', 5'H); 5.65, 5.36, 5.28 (L-Fucα1H); 3.38 (8'H); 2.82 (7'H); 2.02 (D-GalNAc, $CH_3$); 1.30-1.32 (L-Fuc, $CH_3$). The integral of protons of benzene ring to H1 of L-Fuc showed that the reducing terminals of the obtained products were completely reductive ammination by tyrosine.

Example 5

Amino Sulfation 5.1 Materials

Chlorosulfonic acid, tetrabutylammonium hydroxide, dimethyl formamide, pyridine and sodium carbonate and other reagents were commercially available analytical pure.

The deacetylation sample dAFG-1 was prepared from *Stichopus variegates* Semper according to Example 1. The degree of deacetylation was 35%.

5.2 Methods 0.10 g of dAFG-1 was accurately weighed, dissolved in 10 mL of deionized water, adjusted to pH 7.0, reacted in water bath at 40° C. 0.16 g of $Na_2CO_3$ was added one time and 0.20 g of pyridine-chlorosulfonic acid was added within 4 h, after completion of addition, further reacted for 1 hour. At the end of the reaction, the reaction solution was placed and cooled to room temperature, adjusted to pH 7.5-8.0, ultra-filtered to remove the salt, and lyophilized. The molar ratio of sulfate group to carboxyl group was determined by conductivity method.

5.3 Results

The yield of the reaction products was about 87%, calculated by weight. The the molar ratio of sulfate groups to carboxyl groups was 4.3 as determined by conductivity method. It can be seen by the comparison with the native product that the free amino groups were substantially sulfated after deaceylation.

Example 6

Study on Anticoagulant Activity of aTFG 6.1 Materials aTFG sample: A series of aTFG samples with different molecular weights were prepared according to the methods of Examples 2 and 3. The physicochemical properties of these samples are shown in Table 4.

Reagents and instruments: coagulation control plasma, activated partial thromboplastin time (APTT) kit, $CaCl_2$ were manufactured by German TECO GmbH company; other reagents were commercially available and analytical pure. MC-4000 coagulometer (MDC company, Germany).

TABLE 4

Series of aTFG samples with different molecular weights and physicochemical properties

| Sample No. | Weight average molecular weight Mw (Daltons) | Number average molecular weight Mn (Daltons) | Polydispersity index | Molar ratio of sulfate groups to carboxyl groups |
|---|---|---|---|---|
| aTFG-1 | 24866 | 13514 | 1.84 | 3.60 |
| aTFG-2 | 17471 | 9815 | 1.78 | 3.48 |
| aTFG-3 | 12567 | 11321 | 1.11 | 3.12 |
| aTFG-4 | 11332 | 7358 | 1.54 | 3.24 |
| aTFG-5 | 10497 | 6439 | 1.63 | 3.42 |
| aTFG-6 | 9476 | 6402 | 1.48 | 3.34 |
| aTFG-7 | 7000 | 5147 | 1.36 | 3.54 |
| aTFG-8 | 6600 | 4748 | 1.39 | 3.34 |
| aTFG-9 | 5000 | 4166 | 1.20 | 3.42 |

6.2 Methods

5 μL of the sample to be tested was dissolved in Tris-HCl buffer and added in 45 μL coagulation control plasma, used as test sample. Activated partial thromboplastin time (APTT) kit was used to test the coagulation time.

6.3 Results (see Table 5)

TABLE 5

APTT of aTFG with different molecular weights

| Tested sample | Curve equation | Correlation coefficient ($R^2$) | Drug concentration for doubling APTT (μg/mL) |
|---|---|---|---|
| aTFG-1 | y = 11.577x + 31.603 | 0.9939 | 3.40 |
| aTFG-2 | y = 9.0491x + 30.793 | 0.9880 | 3.55 |
| aTFG-3 | y = 6.134x + 37.004 | 0.9849 | 4.22 |
| aTFG-4 | y = 5.756x + 35.005 | 0.9971 | 4.85 |
| aTFG-5 | y = 6.6247x + 37.21 | 0.9958 | 4.92 |
| aTFG-6 | y = 5.3358x + 37.032 | 0.9978 | 6.14 |
| aTFG-7 | y = 4.5807x + 38.73 | 0.9925 | 6.78 |
| aTFG-8 | y = 4.0239x + 38.378 | 0.9874 | 7.81 |
| aTFG-9 | y = 2.5692x + 37.982 | 0.9874 | 12.38 |

The results of table 5 showed that the deaminative depolymerization products of FGAG, aTFG, can significantly prolong the APTT of human plasma, and the drug concentrations for doubling APTT were all less than 12 μg/ml, indicating that the derivatives can effectively inhibit the intrinsic coagulation. By comparing the molecular weights of these derivatives and the drug concentrations required for doubling APTT, it was found that the larger molecular weight related to the stronger anticoagulant activity. Molecular weight is one of the main factors that affect the anticoagulant activity. According to this regular result, considering from retaining hematological activity of FGAG, the preferred aTFG of the present invention has a molecular weight of not less than 5,000 Daltons, based on weight average molecular weight.

Example 7

Inhibitory Activity for Intrinsic Factor Xase 7.1 Materials

The aTFG sample was prepared according to the method of Example 2, with a molecular weight of 8,777 Daltons.

Reagents and Equipment:

Factor VIII (f.VIII), 200 IU/vial, Shanghai RAAS Blood Products Co., Ltd.; f.VIII test kit, Reagents: R1: Human Factor X; R2: Activation Reagent, human Factor IXa, containing human thrombin, calcium and synthetic phospholipids; R3: SXa-11, Chomogenic substrate, specific for Factor Xa; R4: Tris-BSA Buffer; manufactured by HYPHEN BioMed (France). Bio Tek-ELx 808 Microplate reader (American).

7.2 Methods

Determination of the inhibitory activity for intrinsic factor Xase (anti-f.Xase): The detection method established by f.VIII detection kit in conjunction with f.VIII reagent was used. 30 μl of the solution to be tested with series of concentrations or blank control solution (Tris-BSA buffer R4) was mixed with 2.0 IU/ml factor VIII (30 μl), added with the kit reagents R2(30 μl), R1 (30 μl), incubated at 37° C. for 2 minutes; then added with R3 (30 μl), incubated at 37° C. for another 2 minutes, then added with 20% acetic acid (30 μl) to terminate the reaction. $OD_{405nm}$ was detected. DOD was calculated according to the blank control (R4). $EC_{50}$ values of f.Xase inhibition of the samples were calculated according to the formula disclosed in the reference (Sheehan J. P. & Walke E. K., *Blood,* 2006, 107:3876-3882).

7.3 Results

Figure 7:
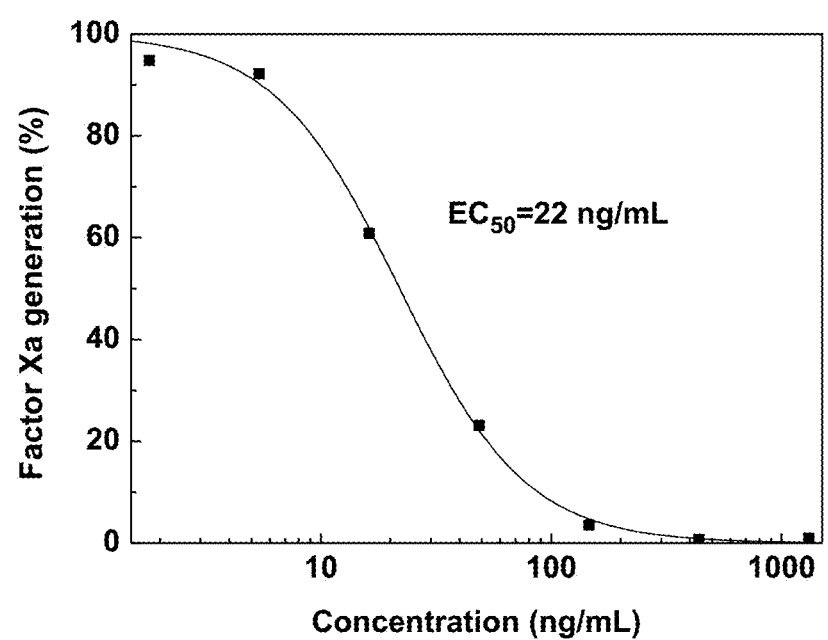
FIG. 7 is the activity of aTFG for inhibiting intrinsic factor Xase.

As shown in FIG. 7., the data showed that the aTFG had an $EC_{50}$ of 22 ng/mL, indicating that it had potent anti-f.Xase activity. Since intrinsic factor Xase is the last enzymatic site in the intrinsic coagulation pathway, and is the rate limiting site of the coagulation process induced by many factors, therefore, the drugs that target at this site have the least influence on physiological coagulation and hemostasis (*Blood,* 2010, 116(22), 4390-4391; *Blood,* 2009, 114, 3092-3100).

Example 8

Freeze-Dried Products 8.1 Materials

According to the methods of Examples 1 and 2, FGAG from *Holothuria scabra* was prepared to obtain aTFG, having a weight average molecular weight of 9,476 Daltons.

8.2 Formula:

| Name of raw materials and excipient | Dosage |
|---|---|
| aTFG-4 | 50 g |
| Water for injection | 500 mL |
| Prepared into | 1000 vials |

8.3 Preparation Process:

Process Procedure:

The formulated aTFG was weighed, added with water for injection to full capacity, stirred to dissolve completely, and subjected to interval autoclaving sterilization. 0.6% pharmaceutical activated carbon was added and stirred for 20 minutes. A Buchner funnel and a 3.0 μm micro porous filter membrane were used for decarbonization filtration to remove pyrogens. The content of the intermediate was tested. The qualified products were passed through a 0.22 μm micro-porous filter membrane; filled into penicillin bottles, 0.5 mL for each bottle, monitoring the filling volume during filling; partially stoppered, and transported into the lyophilizer, lyophilized according to the predetermined freeze-drying curve; completely stoppered, withdrawn from the lyophilizer, capped, inspected to be qualified, obtained the final products.

Lyophilization Procedure:

The samples were placed into the lyophilizer; the temperature of shelves was dropped to −40° C., maintaining for 3 hours; the temperature of cold trap was dropped to −50° C.; then the vacuum was pumped to 300 Oar. Sublimation: the temperature was increased uniformly to −30° C. within 1 hour, maintaining for 2 hours; increased uniformly to −20° C. within 2 hours, maintaining for 8 hours; the vacuum was maintained at 200-300 Oar. Drying: the temperature was increased to −5° C. within 2 hours, maintaining for 2 hours, and the vacuum was maintained at 150-200 μbar; the temperature was increased to 10° C. within 0.5 hour, maintaining for 2 hours, and the vacuum was maintained at 80-100 μbar.; the temperature was increased to 40° C. within 0.5 hour, maintaining for 4 hours, and the vacuum was reduced to the lowest.

What is claimed is:

1. A low-molecular-weight glycosaminoglycan derivative or a pharmaceutically acceptable salt thereof, wherein
monosaccharide compositions of the low-molecular-weight glycosaminoglycan derivative comprise hexuronic acid, hexosamine, deoxyhexamethylose and 2, 5-anhydrated talose or a reduced derivative thereof; the hexuronic acid is D-β-glucuronic acid, the hexosamine is 2-N-acetamino-2-deoxy-D-β-galactose or 2-amino-2-deoxy-D-β-galactose or -β-D-2-sulfated amino-2-deoxygalactose, the deoxyhexamethylose is L-α-fucose, the reduced derivative of 2, 5-anhydrated talose is 2,5-anhydrated talitol or 2,5-anhydrated talosamine or N-substituted-2,5-anhydrated talosamine;
based on molar ratio, the ratio of monosaccharide component content of the low-molecular-weight glycosaminoglycan derivative is hexuronic acid: hexosamine:deoxyhexamethylose=1:(1±0.35):(1±0.3); based on molar ratio, the ratio of 2, 5-anhydrated talose and/or the reduced derivative thereof is not less than 3.0% of the total monosaccharide compositions;
wherein the low-molecular-weight glycosaminoglycan derivative has a weight average molecular weight (Mw) ranging from 5,000 Daltons to 12,000 Daltons, and the low-molecular-weight glycosaminoglycan derivative has a polydispersity index of between 1.1 and 1.5;
further wherein the low-molecular-weight glycosaminoglycan derivative is a mixture of the homologous glycosaminoglycan derivatives having a structure of Formula (I),

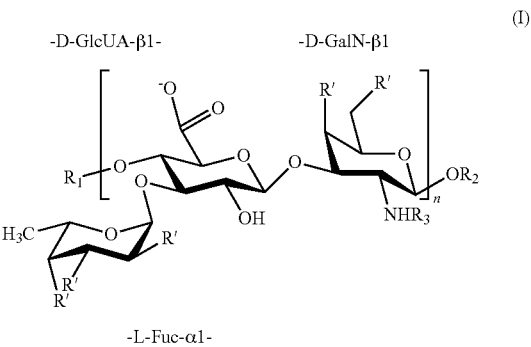

in Formula (I):
n is an integer with an average value of 3-21;
-D-GlcUA-β1- is -β-D-glucuronic acid-1-yl;

-D-GalN-β1- is -β-D-2-acetylamino-2-deoxygalactose-1-yl or -β-D-2-amino-2-deoxygalactose or -β-D-2-sulfated amino-2-deoxygalactose;

L-Fuc-α1- is α-L-fucose-I-yl;

$R_1$ is —H or β-D-2-acetylamino-2-deoxygalactose sulfate-1-yl;

R' is —OH or $OSO_3^-$;

$R_3$ is —H, —$SO_3^-$ or acetyl;

$R_2$ is a group shown in Formula (II):

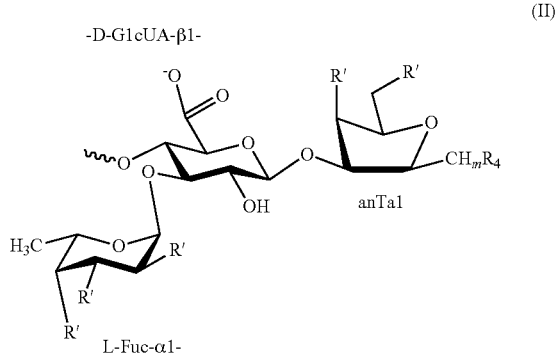

(II)

in Formula (II), -D-GlcUA-β1-, L-Fuc-α1-, and R' are defined as above;

anTal is 2,5-anhydrated talose, the alditol, glycosylamine or N-substituted glycosylamine thereof;

m is 1 or 2;

R4 is optionally =O, —O, —$NH_2$, —$NHR_5$, wherein $R_5$ is C1-C6 straight chain or branched alkyl groups, C7-C12 aryl.

2. The low-molecular-weight glycosaminoglycan derivative or a pharmaceutically acceptable salt thereof according to claim 1, wherein the pharmaceutically acceptable salt is an alkali metal salt or an alkaline-earth metal salt or an organic ammonium salt of the low-molecular-weight glycosaminoglycan derivative.

3. The low-molecular-weight glycosaminoglycan derivative or a pharmaceutically acceptable salt thereof according to claim 2, wherein the pharmaceutically acceptable salt is sodium salt, potassium salt or calcium salt of the low-molecular-weight glycosaminoglycan derivative.

4. The low-molecular-weight glycosaminoglycan derivative or a pharmaceutically acceptable salt thereof according to claim 1, wherein the low-molecular-weight glycosaminoglycan derivative is a deaminative depolymerization product of the fucosylated glycosaminoglycan from body wall and/or viscera of an echinoderm of the class Holothuroidea, or a derivative of the depolymerization product with reduction at the reducing terminal.

5. The low-molecular-weight glycosaminoglycan derivative or a pharmaceutically acceptable salt thereof according to claim 1, wherein the preparation method comprises the following steps of:

Step 1: treating fucosylated glycosaminoglycan from an echinoderm with hydrazine, subjecting the hexosamine therein to partial deacetylation reaction, to obtain a partially deacetylated product of the fucosylated glycosaminoglycan;

wherein in Step 1, the fucosylated glycosaminoglycan from an echinoderm refers to native fucosylated glycosaminoglycan products extracted and purified from the body wall and/or viscera of an echinoderm of the class Holothuroidea; the monosaccharide components of the fucosylated glycosaminoglycan comprise D-glucuronic acid, D-N-acetylamino-2-deoxygalactose and L-fucose; the echinoderm of the class Holothuroidea is selected from the groups consisting of *Thelenota ananas* Jaeger, *Stichopus variegates* Semper, *Holothuria scabra* Jaeger, *Holothuria leucospilota* Brandt, *Holothuria edulis* Lesson, *Bohadschia argus* Jaeger, *Stichopus chloronotus* Brandt, *Holothuria sinica* Liao, *Acaudina molpadioides* Semper, *Pearsonothuria graeffei* Semper and *Holothuria nobilis* Selenka;

wherein in Step 1, the method of deacetylation reaction treated with hydrazine comprises adding the fucosylated glycosaminoglycan from an echinoderm into anhydrous hydrazine or hydrazine hydrate solution, reacting at the temperature of 75° C.-125° C. for 2-14 hours under stirring in the presence or absence of a catalyst;

further in Step 1, the deacetylation reaction treated with hydrazine is carried out in the presence of a catalyst, the catalyst is optionally selected from the groups consisting of hydrazine sulfate, hydrazine hydrochloride, hydrochloric acid or sulfuric acid, and the catalyst in the reaction solution has a concentration of 0.5%-2.5%;

Step 2: treating the partially deacetylated product of the fucosylated glycosaminoglycan obtained in Step 1 with nitrous acid, subjecting it to deamination and depolymerization, to obtain a low-molecular-weight fucosylated glycosaminoglycan with 2, 5-anhydrotalosyl as a reducing terminal; optionally, subjecting the reducing terminal of the obtained low-molecular-weight fucosylated glycosaminoglycan to reduction reaction, comprising reducing 2, 5-anhydrotalosyl into an alditol, glycosylamine or N-substituted glycosylamine;

wherein in Step 2, the method of the deaminative depolymerization treated with nitrous acid comprises: in ice bath or at room temperature, adding the partially deacetylated product of the fucosylated glycosaminoglycan obtained in Step 1 into 4-6 mol/L nitrous acid solution with a pH 1-5, reacting for 5-60 minutes followed by adding an alkaline solution to adjust pH to 8 or above to terminate the reaction; and then optionally process:

(1) adding 3-5 volumes of ethanol to the reaction solution, standing still, centrifuging to obtain precipitation, purifying the obtained precipitation by ultrafiltration or chromatography;

(2) reducing 2, 5-anhydrotalose, the reducing terminal of the reaction product, into an alditol by sodium borohydride or sodium cyanoborohydride, and then purifying the obtained product according to the procedure of Step (1);

(3) reducing 2, 5-anhydrotalose, the reducing terminal of the reaction product, into a glycosylamine or N-substituted glycosylamine through reductive amination reaction, and then purifying the obtained products according to the procedure of Step (1).

6. A pharmaceutical composition comprising an anticoagulant effective amount of the low-molecular-weight glycosaminoglycan derivative or a pharmaceutically acceptable salt thereof according to claim 1, and a pharmaceutically acceptable excipient.

7. The pharmaceutical composition according to claim 6, wherein the dosage form of the pharmaceutical composition is water solution for injection or lyophilized powder for injection.

* * * * *